(12) United States Patent
Konaka

(10) Patent No.: US 10,296,725 B2
(45) Date of Patent: May 21, 2019

(54) STRUCTURE REFINING APPARATUS, METHOD AND PROGRAM

(71) Applicant: RIGAKU CORPORATION, Tokyo (JP)

(72) Inventor: Hisashi Konaka, Hamura (JP)

(73) Assignee: RIGAKU CORPORATION, Tokyo (JP)

( * ) Notice: Subject to any disclaimer, the term of this patent is extended or adjusted under 35 U.S.C. 154(b) by 1203 days.

(21) Appl. No.: 14/323,666

(22) Filed: Jul. 3, 2014

(65) Prior Publication Data

US 2015/0227643 A1 Aug. 13, 2015

(30) Foreign Application Priority Data

Feb. 12, 2014 (JP) .................................. 2014-024745

(51) Int. Cl.
*G06F 19/00* (2018.01)

(52) U.S. Cl.
CPC ........ *G06F 19/701* (2013.01); *C07B 2200/13* (2013.01)

(58) Field of Classification Search
None
See application file for complete search history.

(56) References Cited

U.S. PATENT DOCUMENTS 6,668,040 B2 * 12/2003 Cederstrom ............. G21K 1/06
378/84

8,957,114 B2 * 2/2015 Laughlin ............... A61K 9/2018
514/647
2003/0198997 A1 * 10/2003 Von Dreele .......... G01N 23/207
435/7.1

OTHER PUBLICATIONS

D. Watkin, "Structure refinement: some background theory and practical strategies" pp. 491-522, 2008.*
MIT OpenCourseWare "5.069 Crystal Structure Analysis" Spring 2008, pp. 1-29.*
P. Muller, "Practical suggestions for better crystal structures", Mar. 2009, pp. 57-83.*
Immirizi, "Constraints and restraints in crystal structure analysis", Journal of Applied Crystallography, vol. 42, pp. 362-364, 2009.
Waser, "Least-Squares Refinement with Subsidiary Conditions", Acta Cryst., vol. 16, pp. 1091-1094, 1963.

* cited by examiner

*Primary Examiner* — Kibrom K Gebresilassie
(74) *Attorney, Agent, or Firm* — Birch, Stewart, Kolasch & Birch, LLP

(57) ABSTRACT

To provide a structure refining apparatus, a method and a program capable of univocally and appropriately setting a restraint with a statistically feasible intensity and specifying a crystal structure model making use of a measurement result under a constraint condition to reasonable known data. A structure refining apparatus 100 adjusting the crystal structure model on the basis of the measurement result and the known data includes a restraint applying unit 120 configured to apply the restraint such that a divergence between a parameter specifying a crystal structure and a known representative value becomes equivalent to a standard uncertainty of the known representative value and a structure specifying unit 140 configured to specify the crystal structure model on the basis of the measurement result under the applied restraint.

6 Claims, 19 Drawing Sheets

0$^{th}$ cycle

$$R^{(0)} = R_{wp}^{(0)} + s_{res}^{(0)} \left( R_{res}^{d\,(0)} + R_{res}^{a\,(0)} \right), \quad s_{res}^{(0)} = 1$$

$$\sigma^{(0)} = \sqrt{\frac{1}{M+N} \left[ R_{res}^{d\,(0)} + R_{res}^{a\,(0)} \right]}$$

$$\Delta\sigma^{(0)} = (\sigma^{(0)} - 1)$$

$$s_{res}^{(1)} = s_{res}^{(0)} - \left(\frac{ds}{d\sigma}\right)^{(0)} \Delta\sigma^{(0)}, \quad \left(\frac{ds}{d\sigma}\right)^{(0)} = -1$$

1$^{st}$ cycle

$$R^{(1)} = R_{wp}^{(1)} + s_{res}^{(1)} \left( R_{res}^{d\,(1)} + R_{res}^{a\,(1)} \right)$$

$$\sigma^{(1)} = \sqrt{\frac{1}{M+N} \left[ R_{res}^{d\,(1)} + R_{res}^{a\,(1)} \right]}$$

$$\Delta\sigma^{(1)} = (\sigma^{(1)} - 1)$$

$$s_{res}^{(2)} = s_{res}^{(1)} - \left(\frac{ds}{d\sigma}\right)^{(1)} \Delta\sigma^{(1)}, \quad \left(\frac{ds}{d\sigma}\right)^{(1)} = \frac{s_{res}^{(1)} - s_{res}^{(0)}}{\sigma^{(1)} - \sigma^{(0)}}$$

⋮ n$^{th}$ cycle

$$R^{(n)} = R_{wp}^{(n)} + s_{res}^{(n)} \left( R_{res}^{d\,(n)} + R_{res}^{a\,(n)} \right)$$

$$\sigma^{(n)} = \sqrt{\frac{1}{M+N} \left[ R_{res}^{d\,(n)} + R_{res}^{a\,(n)} \right]}$$

$$\Delta\sigma^{(n)} = (\sigma^{(n)} - 1)$$

$$s_{res}^{(n+1)} = s_{res}^{(n)} - \left(\frac{ds}{d\sigma}\right)^{(n)} \Delta\sigma^{(n)}, \quad \left(\frac{ds}{d\sigma}\right)^{(n)} = \frac{s_{res}^{(n)} - s_{res}^{(n-1)}}{\sigma^{(n)} - \sigma^{(n-1)}}$$

FIG.4

Cycle 1: $s_{res} = 1.0000$
$\sigma_{Norm} = 4.9046$

Cycle 3: $s_{res}$ = 14.2731
$\sigma_{Norm}$ = 2.2072

Cycle 4: $s_{res}$ = 21.5757
$\sigma_{Norm}$ = 1.8540

Cycle 5: $s_{res}$ = 39.2279
$\sigma_{Norm}$ = 1.2874

Cycle 6: $s_{res}$ = 48.1845
$\sigma_{Norm}$ = 1.1975

Cycle 7: $s_{res}$ = 67.8599
$\sigma_{Norm}$ = 1.0290

Cycle 8: $s_{res}$ = 71.2511
$\sigma_{Norm}$ = 1.0034

O3–C21 INTERATOMIC DISTANCE
TARGET VALUE= 1.2255 A
STANDARD UNCERTAINTY= 0.0309A

C9–C10–C14 ANGLE
TARGET VALUE= 119.61°
STANDARD UNCERTAINTY= 1.37°

| NUMBER OF CYCLES | O3-C21 INTERATOMIC DISTANCE (REPRESENTATIVE VALUE = 1.2255 Å) | C9-C10-C14 ANGLE (REPRESENTATIVE VALUE = 119.61°) |
|---|---|---|
| 1 | 1.00187 | 97.11 |
| 2 | 1.05357 | 105.00 |
| 3 | 1.18143 | 113.61 |
| 4 | 1.20331 | 115.05 |
| 5 | 1.22817 | 117.35 |
| 6 | 1.23243 | 117.67 |
| 7 | 1.23808 | 118.25 |
| 8 | 1.23864 | 118.33 |

FIG.9

STRUCTURE REFINING APPARATUS, METHOD AND PROGRAM

BACKGROUND OF THE INVENTION

Field of the Invention

The present invention relates to a technology for refining a structure by using a restraint.

Description of the Related Art

In analysis of a crystal structure, there are cases where a method of specifying a crystal structure model which best fits measurement data by using the method of least squares is adopted. If measurement data of low quality is used in such a method, a result which is not chemically reasonable may be obtained in some cases. However, it is possible to cope with this situation by setting weak constraint conditions (restraints) on an interatomic bond distance and an interatomic bond angle (see Jurg Waser, "Least-Squares Refinement with Subsidiary Conditions", Acta Cryst, 1963, Vol. 16, P1091).

However, if the set restraint is too strong, analysis that the measurement data has been disregarded may be obtained. Setting of the restraint has been performed on the basis of individual judgment so far (see Attilio Immirzi, "Constraints and restraints in crystal structure Analysis", Journal of Applied Crystallography, 2009, Vol. 42, P362-364). For example, setting of the restraint may be performed intensely in order to perform analysis that importance has been attached to a chemically reasonable crystal structure in some cases. In addition, the restraint may be set such that the bond distance and bond angle which are remarkably different from those of a known crystal structure which is partially similar to the crystal structure concerned have reasonable values in other cases.

If the intensity of the restraint in structure refinement is adjusted on the basis of individual decision as mentioned above, it may sometimes occur that the chemically reasonable crystal structure is not obtained and/or analysis that the measurement data has been disregarded is performed. Absence of an index for appropriate restraint intensity may be one of the causes of occurrence of such situations.

SUMMARY OF THE INVENTION

The present invention has been made in view of the above-mentioned circumstances and has an object to provide a structure refining apparatus, a method and a program capable of univocally and appropriately setting a restraint with a statistically feasible intensity and specifying a crystal structure model making use of a measurement result under a constraint condition to reasonable known data.

(1) In order to attain the above-mentioned object, a structure refining apparatus according to an embodiment of the present invention is one that adjusts a crystal structure model on the basis of a measurement result and known data, comprising: a restraint applying unit configured to apply a restraint such that a divergence between a parameter specifying a crystal structure and a known representative value becomes equivalent to a standard uncertainty of the known representative value; and a structure specifying unit configured to specify the crystal structure model on the basis of the measurement result under the applied restraint.

Thus, it is possible to set the restraint univocally and appropriately with the statistically feasible intensity and to specify the crystal structure making use of the measurement result under the constraint condition to the reasonable known data.

(2) In addition, in the structure refining apparatus according to the embodiment of the present invention, the restraint applying unit calculates a $\sigma_{Norm}$ value from a value obtained by normalizing the divergence between the parameter and the representative value by the standard uncertainty and determines contribution of a restraint term indicating a residual relative to the representative value so as to bring the $\sigma_{Norm}$ value close to one, and wherein the structure specifying unit specifies the crystal structure model adapted to minimize a total residual to which the restraint term has been added with the determined contribution to an evaluation value term indicated by a weighted residual relative to a measured value. Thus, it is possible to readily calculate the reasonable contribution of the restraint terms and to calculate the reasonable crystal structure model under the above-mentioned condition.

(3) In addition, in the structure refining apparatus according to the embodiment of the present invention, the restraint applying unit determines contribution of the restraint term on the assumption that the divergence between the parameter and the known representative value relative to the standard uncertainty of the known representative value has a linear relation with contribution of the restraint term.

Thus, it is possible to readily and accurately determine contribution of the restraint term.

(4) In addition, the structure refining apparatus according to the embodiment of the present invention further includes a decision unit configured to decide whether or not the divergence between the parameter and the known representative value relative to the standard uncertainty of the known representative value has approached within a predetermined range of a target value, wherein the decision unit makes the restraint applying unit and the structure specifying unit repetitively perform application of the restraint and specification of the crystal structure model until it is decided that the divergence has approached the predetermined range. Thus, it is possible to specify the reasonable crystal structure model by automatically determining the statistically feasible restraint intensity by performing loop calculation.

(5) The structure refining apparatus according to the embodiment of the present invention further includes a representative value holding unit configured to acquire data on the representative value and a statistical uncertainty thereof from an external database through a network and to hold the data, wherein the restraint applying unit calculates the restraint to be applied by using the held data on the representative value and the statistical uncertainty thereof. Thus, it is possible to calculate the reasonable restraint by using highly reliable data which is made public to the outside.

(6) In addition, a method according to an embodiment of the present invention is a structure refining method which adjusts a crystal structure model on the basis of a measurement result and known data, comprising the steps of: applying a restraint such that a divergence between a parameter specifying a crystal structure and a known representative value becomes equivalent to a statistical uncertainty of the known representative value; and specifying the crystal structure model on the basis of the measurement result under the applied restraint.

Thus, it is possible to set the restraint univocally and appropriately with a statistically feasible intensity and to specify the crystal structure model making use of the measurement result under a constraint condition to the reasonable known data.

(7) In addition, a program according to an embodiment of the present invention is a program for structure refinement which adjusts a crystal structure model on the basis of a measurement result and known data and causes a computer to execute a series of processes including the processes of: applying a restraint such that a divergence between a parameter specifying a crystal structure and a known representative value becomes equivalent to a statistical uncertainty of the known representative value; and specifying the crystal structure model on the basis of the measurement result under the applied restraint.

Thus, it is possible to set the restraint univocally and appropriately with a statistically feasible intensity and to specify the crystal structure model making use of the measurement result under a constraint condition to the reasonable known data.

According to the embodiments of the present invention, it becomes possible to set the restraint univocally and appropriately with the statistically feasible intensity and to specify the crystal structure model making use of the measurement result under the constraint condition to the reasonable known data.

BRIEF DESCRIPTION OF THE DRAWINGS

FIG. 4 includes diagrams illustrating one example of calculation in an n-th cycle.

FIG. 9 is a table illustrating one example of transition of the bond distance of O3-C21 and the bond angle of C9-C10-C14 relative to the number of cycles.

DETAILED DESCRIPTION OF THE INVENTION

Figure 1A:
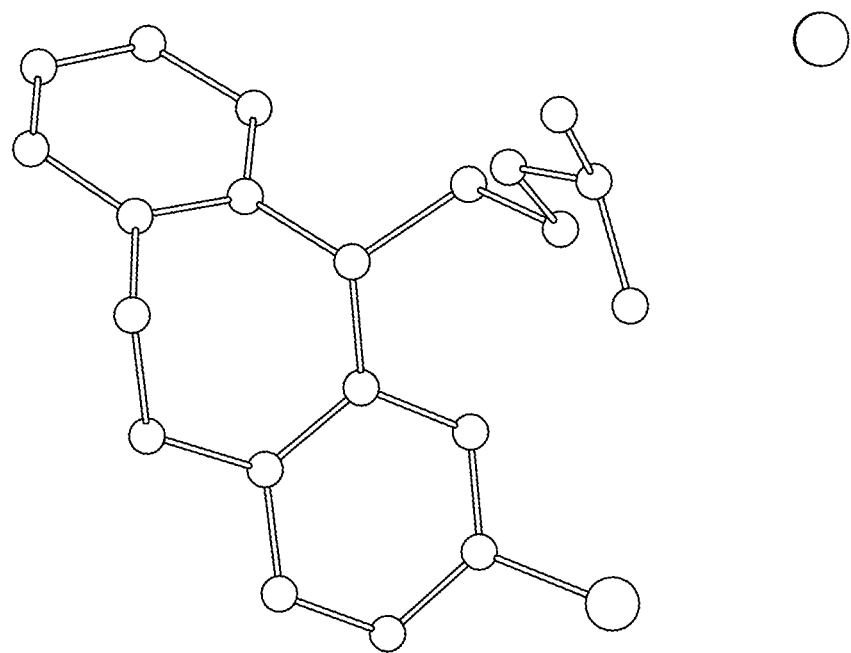
FIG. 1A is a diagram illustrating one example of a crystal structure model calculated by applying a restraint.

Next, an embodiment of the present invention will be described with reference to the accompanying drawings. For facilitating understanding of the description, the same reference numerals are assigned to the same constitutional elements in the respective drawings and redundant description is omitted.

(Principle of Determining Contribution of Restraint Term)

In crystal structure refinement by the method of least squares, values of various parameters are determined such that measurement data match calculation data calculated from the various parameters as much as possible. In that case, the parameters that give the minimum evaluation value (for example, $R_{wp}$) indicating a degree of matching between the measurement data and the calculation data are determined.

Figure 1B:
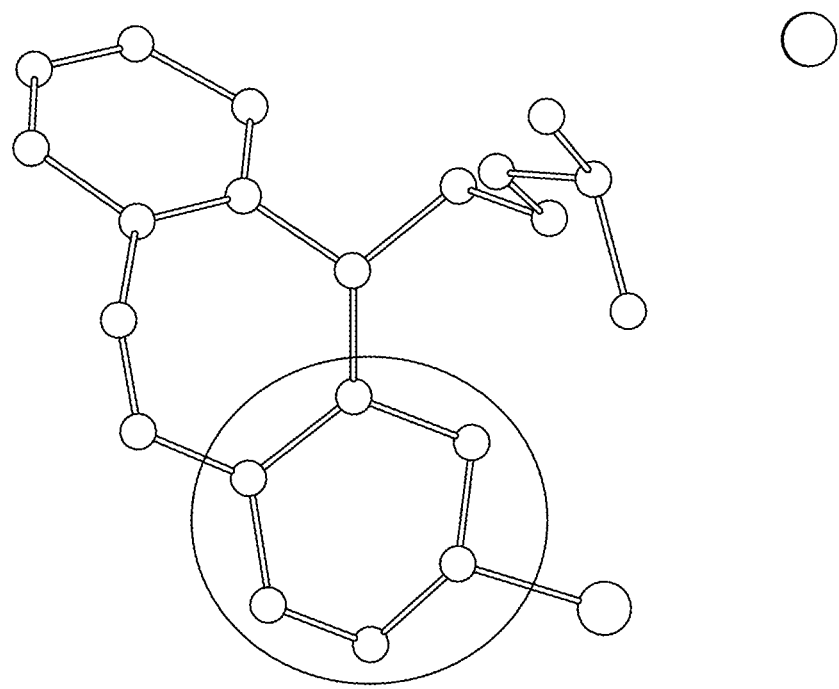
FIG. 1B is a diagram illustrating one example of a crystal structure model calculated without applying the restraint.

In a case where the restraint is to be taken into account in the crystal structure refinement, the parameters are determined such that not $R_{wp}$ but the sum of $R_{wp}$ and a restraint term concerned is minimized. FIG. 1A and FIG. 1B are diagrams respectively illustrating one example of a crystal structure model calculated by applying the restraint and one example of a crystal structure model calculated with no application of the restraint (see the later described Embodiment with respect to the specific condition of FIG. 1A). It is visually confirmed that a benzene ring is distorted in the crystal structure model which has been refined with no application of the restraint (see an encircled part in FIG. 1B).

A representative value such as a median value or a mean value of each of the bond distance and the bond angle and a dispersion (a standard uncertainty) thereof are set for compounds whose partial structures are similar to one another from ever analyzed crystal structures. Whereby, the relative restraint intensity between each bond distance and each bond angle is defined depending on the magnitude of the standard uncertainty of the representative value.

A ratio of a profile-matching-degree-based penalty $R_{wp}$ to a molecular-structure-based penalty $R_{res}$ by restraint setting in the method of least squares is determined such that the dispersion (the standard uncertainty) of a normalized value of each of the parameters such as the bond distance and the bond angle amounts to one.

As a result, it is possible to univocally apply the restraint of statistically appropriate intensity. In addition, this method allows automatic refinement of the crystal structure without depending on the experience of an analyzer. Specifically, it is possible to determine the crystal structure by the method of least squares such that a total residual R expressed by the following numerical formula (1) that restrain terms $R_{res}^{d}$ and $R_{res}^{a}$ of the bond distance and the bond angle are added to a residual sum of squares $R_{wp}$ for the measurement data is minimized.

$$R = R_{wp} + s_{res}(R_{res}^{d} + R_{res}^{a}) \quad (1)$$

Here, $S_{res}$ is a coefficient determining contribution of the restraint term. Setting $S_{res}$ to too large a value leads to disregard of the measurement data and therefore an analysis result which is similar to that obtained when the restraint is set is obtained. However, in analysis of a powder crystal structure, in particular, in a case where an organic matter is to be analyzed, since convergence may occur at an atom position which is low in chemical reasonability unless refinement is performed by setting the restraints for the bond distance and the bond angle, it is necessary to set $S_{res}$ of a certain magnitude.

$R_{res}^d$ and $R_{res}^a$ are expressed by numerical formulae (2) and (3), respectively.

$$R_{res}^d = \sum_i^M \left(\frac{d_{0i} - d_i}{\sigma_i^d}\right)^2 \quad (2)$$

$$R_{res}^a = \sum_j^N \left(\frac{a_{0j} - a_j}{\sigma_j^a}\right)^2 \quad (3)$$

Here, $d_{oi}$ and $\sigma_i^d$ are a representative value (for example, a median (or mean) bond distance of a similar structure) of the bond distance and a standard uncertainty thereof respectively and $a_{oj}$ and $\sigma_j^a$ are a representative value (for example, a median (or mean) bond angle of the similar structure) of the bond angle and a standard uncertainty thereof respectively. In addition, M and N are the number of restraint terms of the bond distance and the number of restraint terms of the bond angle, respectively.

Each of deviations $|(d_{oi}-d_i)/\sigma_i^d|$ and $|(a_{oj}-a_j)/\sigma_j^a|$ from the mean values of analyzed bond distance $d_i$ and bond angle $a_j$ which have been respectively normalized by the standard uncertainties approaches zero as $S_{res}$ is increased and is reduced in dependency on the representative value of the similar compound and generally has a large value as $S_{res}$ is decreased.

As expressed in a numerical formula (4), $S_{res}$ is set such that a normalized standard uncertainty $\sigma_{Norm}$ of dispersions of the above-mentioned values amounts to one.

$$\sigma_{Norm} = \sqrt{\frac{1}{M+N}\left[\sum_i^M \left(\frac{d_{0i} - d_i}{\sigma_i^d}\right)^2 + \sum_j^N \left(\frac{a_{0j} - a_j}{\sigma_j^a}\right)^2\right]} = 1 \quad (4)$$

Incidentally, although the standard uncertainties of both of the bond distance and the bond angle are normalized to be one in the numerical formula (4), it is also possible to separately normalize the respective uncertainties.

With respect to the bond distance and the bond angle of the similar structure and the dispersions thereof, an external database for crystal structures (for example, Cambridge Structural Database (CSD) of Cambridge Crystallographic Data Centre (CCDC), 9. BASIC STRUCTURAL FEATURES of International Tables for Crystallography Volume C and so forth) may be used.

(Configuration of Structure Refining Apparatus)

Figure 2:
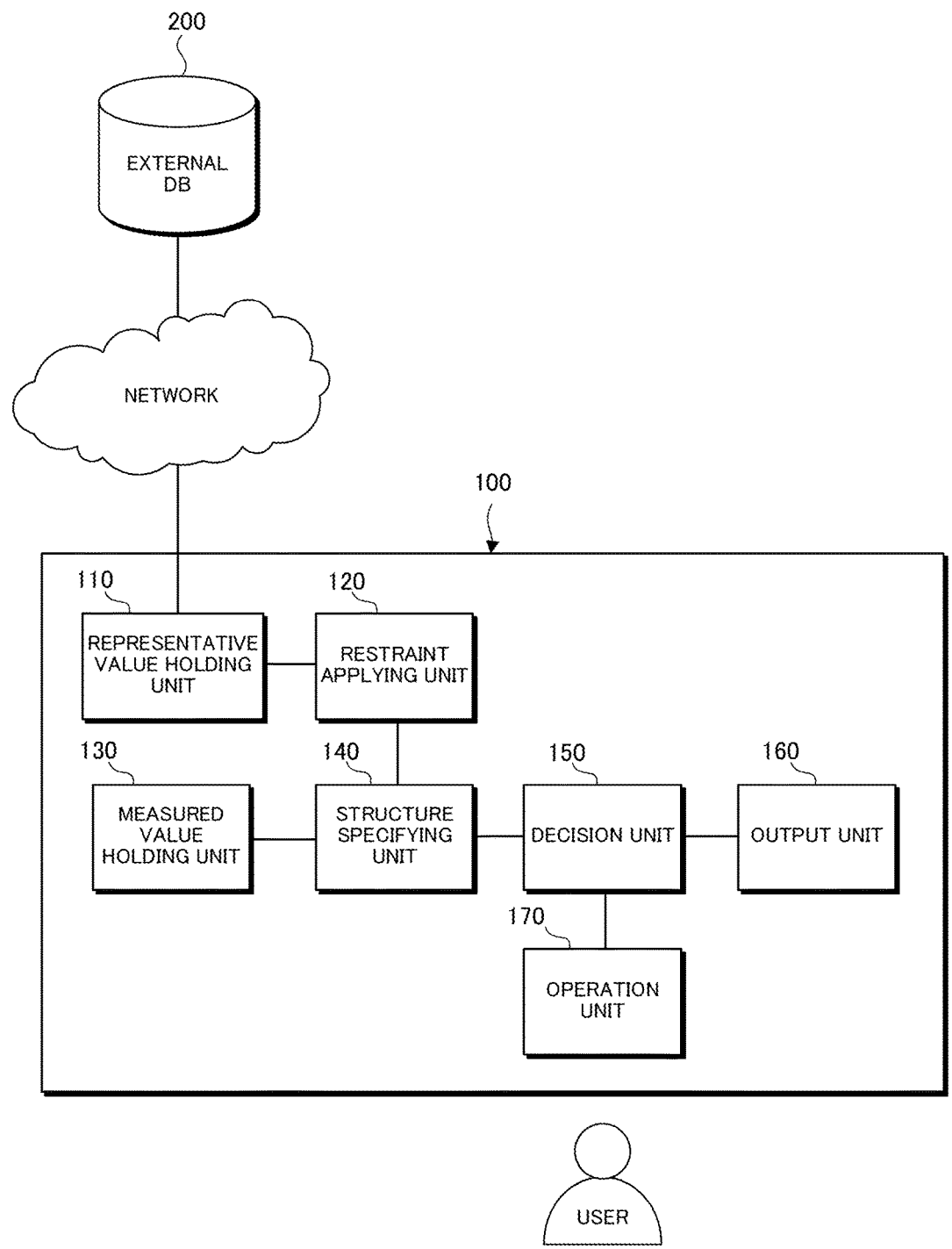
FIG. 2 is a block diagram illustrating one functional configuration example of a structure refining apparatus according to an embodiment of the present invention.

FIG. 2 is a block diagram illustrating one functional configuration example of a structure refining apparatus 100. The structure refining apparatus 100 is a apparatus that adjusts a crystal structure model on the basis of a measurement result and known data and may be configured by using, for example, a PC terminal and so forth. The structure refining apparatus 100 is capable of obtaining a result which would satisfy both of measurement data and a weak constraint condition by applying the restraints to the parameters such as the bond distance and the bond angle and performing refinement by taking not only the measurement data but also the weak constraint condition into account.

As illustrated in FIG. 2, the structure refining apparatus 100 includes a representative value holding unit 110, a restraint applying unit 120, a measured value holding unit 130, a structure specifying unit 140, a decision unit 150, an output unit 160 and an operation unit 170.

The representative value holding unit 110 acquires data on a representative value and a statistical uncertainty thereof from an external database 200 through a network and holds the data. Thus, it is possible to calculate a reasonable restraint by using the highly reliable data which is made public to the outside.

The restraint applying unit 120 applies the restraint such that a divergence between a parameter specifying the crystal structure concerned and the known representative value becomes equivalent to the standard uncertainty of the known representative value. Specifically, the restraint applying unit 120 calculates the $\sigma_{Norm}$ value from a value obtained by normalizing the divergence between the parameter and the representative value by the standard uncertainty by using the data on the representative value and the statistical uncertainty thereof held in the representative value holding unit 110 and determines contribution of the restraint term indicating a residual relative to the representative value such that the $\sigma_{Norm}$ value approaches one.

The restraint applying unit 120 determines contribution of the restraint term on the assumption that the divergence between the parameter and the known representative value relative to the standard uncertainty of the known representative value has a linear relation with contribution of the restraint term. Thus, it is possible to readily and accurately determine contribution of the restraint term.

The measured value holding unit 130 holds measured values of a lattice constant and so forth as a result of measurement and analysis of a diffracted X-ray by single crystal structure analysis and/or powder crystal structure analysis. The held measured values are referred in calculation by the structure specifying unit 140.

The structure specifying unit 140 specifies the crystal structure model on the basis of the result of measurement under the applied restraint. Thus, it is possible to set the restraint univocally and appropriately with the statistically feasible intensity and to specify the crystal structure model making use of the measurement result under the constraint condition to the reasonable known data.

Specifically, the structure specifying unit 140 specifies the crystal structure model that minimizes a total residual to which the restraint terms have been added with the determined contribution to an evaluation value term indicated by a weighted residual relative to the measured value. Thus, it is possible to readily calculate the reasonable contribution of the restraint terms and to calculate the reasonable crystal structure model under the above-mentioned condition.

The decision unit 150 decides whether or not the divergence between the parameter and the known representative value relative to the standard uncertainty of the known representative value has approached within a predetermined range of a target value. Then, the decision unit 150 makes the restraint applying unit 120 and the structure specifying unit 140 repetitively perform application of the restraint and specification of the crystal structure model until it is decided that the divergence has approached within the predetermined range. Thus, it is possible to specify the reasonable crystal structure model by automatically determining the statistically feasible restraint intensity by cycle calculation.

The output unit 160 outputs data on the crystal structure model specified by the structure specifying unit 140. The operation unit 170 accepts an operation from a user and gives instructions for adjusting execution of processing such as inputting of a threshold value.

(Operation of Structure Refining Apparatus)

Figure 3:
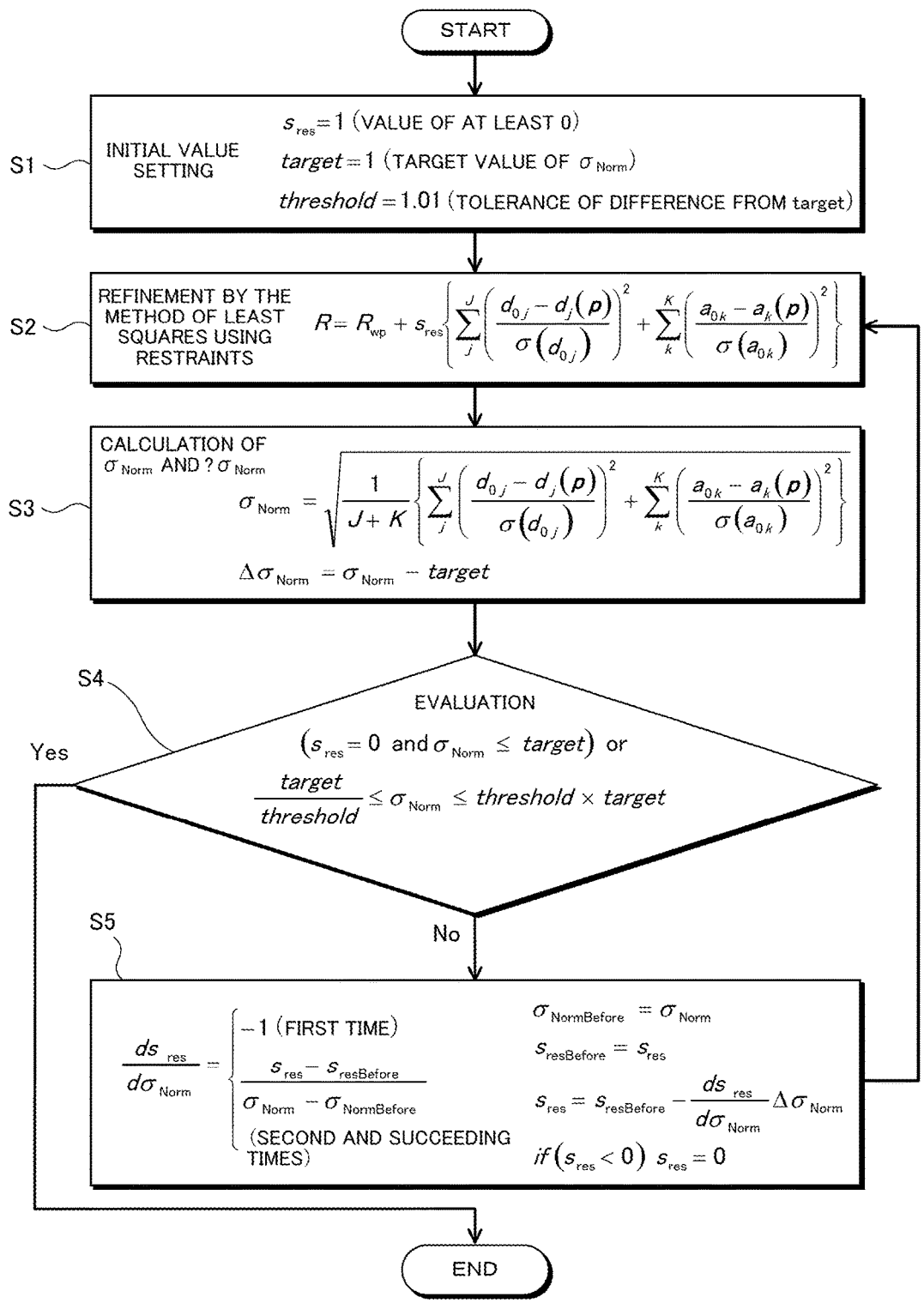
FIG. 3 is a flowchart illustrating one example of an operation of the structure refining apparatus according to the embodiment of the present invention.
Figure 5A:
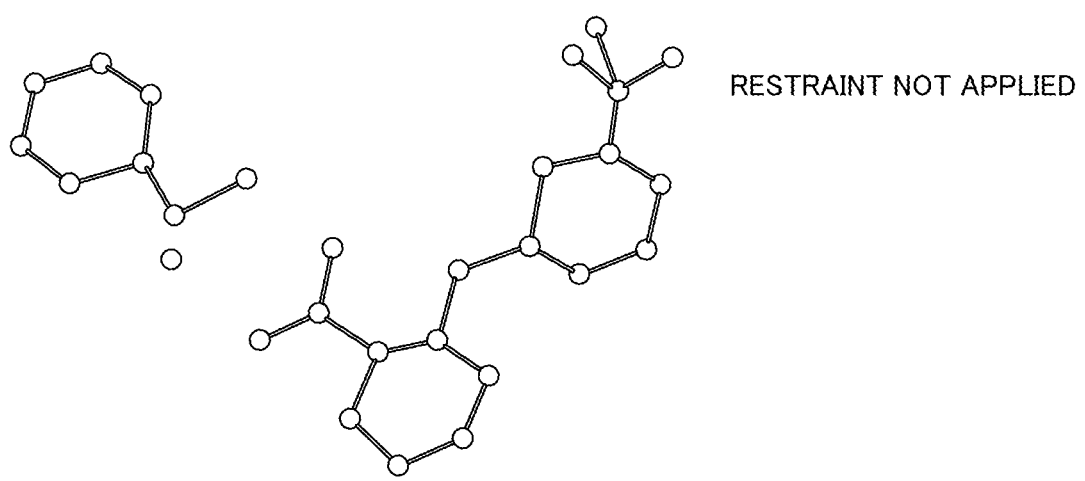
FIG. 5A is a diagram illustrating one example of a crystal structure model of an embodiment without the restraint.
Figure 5B:
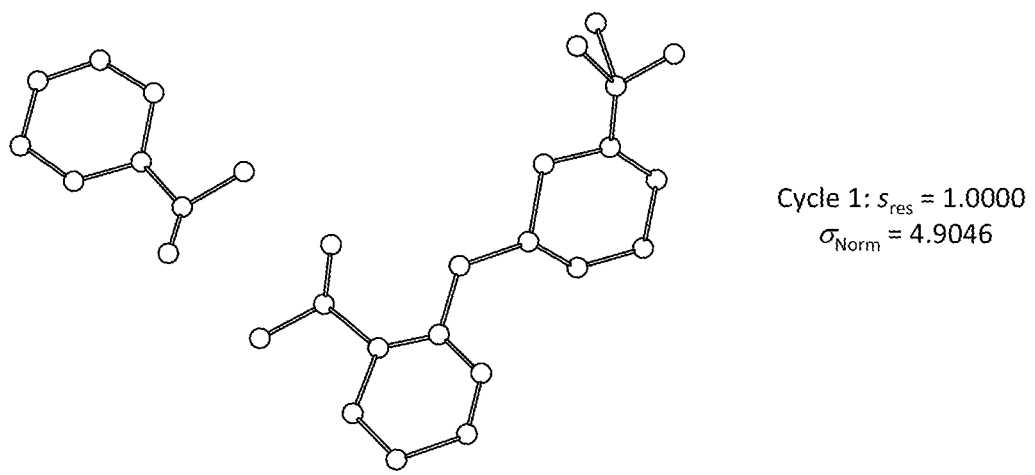
FIG. 5B is a diagram illustrating one example of the crystal structure model of the embodiment at the time of a first cycle.
Figure 5C:
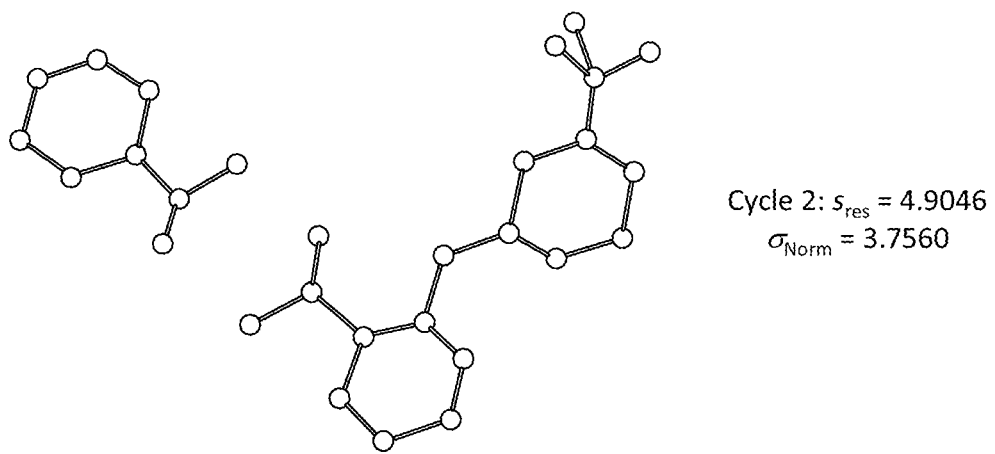
FIG. 5C is a diagram illustrating one example of the crystal structure model of the embodiment at the time of a second cycle.
Figure 5D:
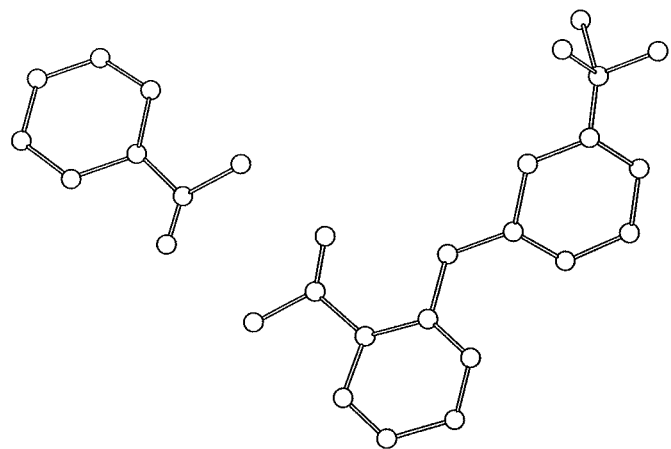
FIG. 5D is a diagram illustrating one example of the crystal structure model of the embodiment at the time of a third cycle.
Figure 5E:
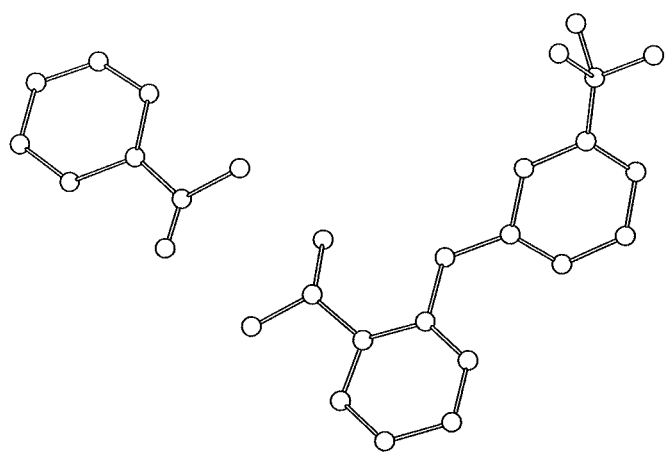
FIG. 5E is a diagram illustrating one example of the crystal structure model of the embodiment at the time of a fourth cycle.
Figure 5F:
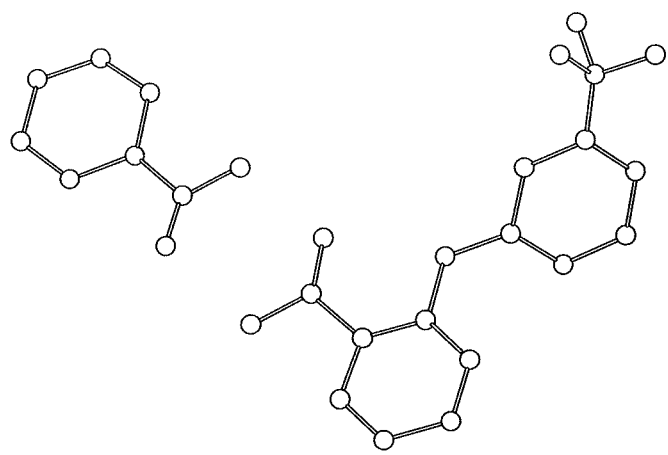
FIG. 5F is a diagram illustrating one example of the crystal structure model of the embodiment at the time of a fifth cycle.
Figure 5G:
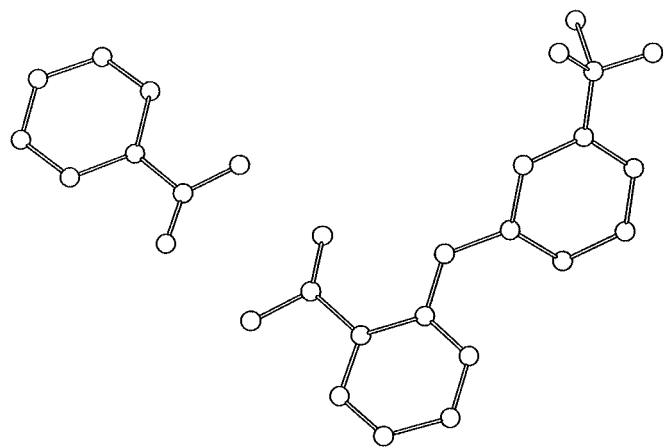
FIG. 5G is a diagram illustrating one example of the crystal structure model of the embodiment at the time of a sixth cycle.
Figure 5H:
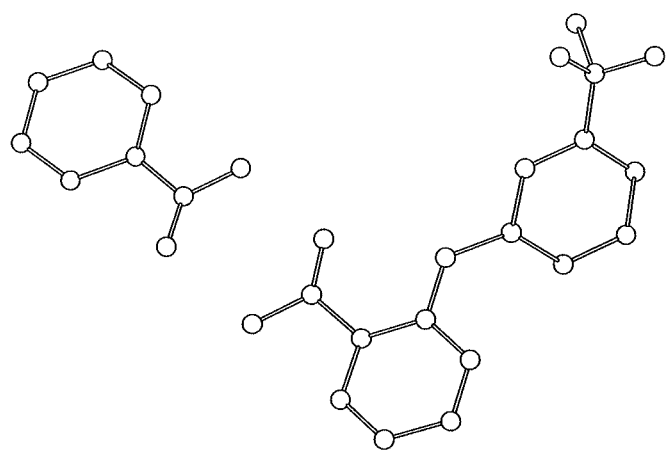
FIG. 5H is a diagram illustrating one example of the crystal structure model of the embodiment at the time of a seventh cycle.
Figure 5I:
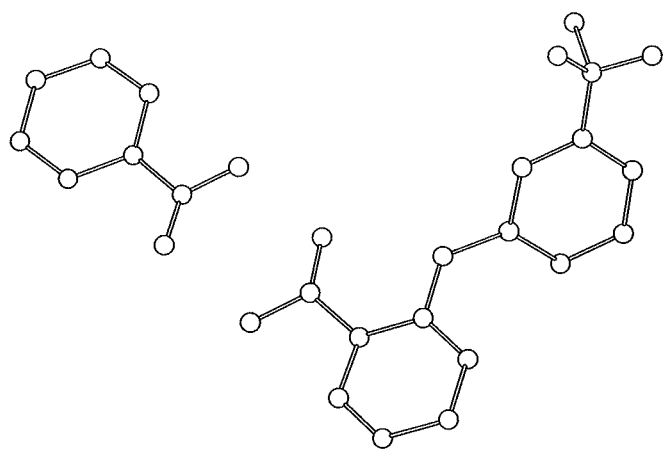
FIG. 5I is a diagram illustrating one example of the crystal structure model of the embodiment at the time of an eighth cycle.

Next, an operation of the structure refining apparatus 100 configured as mentioned above will be described. FIG. 3 is a flowchart illustrating one example of the operation of the structure refining apparatus 100. First, initial values are set (step S1). For example, setting is performed such that $S_{res}=1$, the target value (the target value of $\sigma_{Norm}=1$ and the threshold value (a tolerance of a difference from the target value)=1.01. Incidentally, the initial value of $S_{res}$ may not necessarily be set to one.

Next, refinement by the method of least squares using the restraints is performed (step S2). Whereby, optimum parameters with $S_{res}=1$ are calculated and the crystal structure model is specified. Then, $\sigma_{Norm}$ and $\Delta\sigma_{Norm}$ are calculated from the obtained parameters (step S3). Then, it is decided whether or not $\sigma_{Norm}$ sufficiently approaches the target value on the basis of the calculated $\sigma_{Norm}$ and $\Delta\sigma_{Norm}$ (step S4). For example, it is decided whether or not a condition that $S_{res}=0$ and $\sigma_{Norm}\le$target, or target/threshold$\le\sigma_{Norm}\le$threshold×target is satisfied. Decision may be also made depending on whether $\Delta\sigma_{Norm}$ is not more than a predetermined value in addition to the above-mentioned decision making.

In a case where the condition is not satisfied as a result of decision, $S_{res}$ is changed such that $\sigma_{Norm}$ approaches one (step S5). Specifically, $S_{res}=S_{resbefore}$ (the last value)$-ds_{res}/d\sigma_{Norm}\times\Delta\sigma_{Norm}$ is calculated using $ds_{res}/d\sigma_{Norm}$ and the process returns to step S2. In a case where the condition is satisfied, calculation is terminated.

FIG. 4 includes diagrams illustrating one example of calculation in an n-th cycle. As illustrated in FIG. 4, it is possible to automatically obtain the optimum crystal structure by refining the structure while changing Sres until $\sigma$ reaches a range close to one. Incidentally, it is possible to implement the above-mentioned respective processes by causing a computer of the structure refining apparatus 100 to execute a program. The program can be stored on a computer readable medium.

Embodiment

FIG. 1A is a diagram illustrating one example of a result of refinement performed on the structure of an organic matter (clomipramine hydrochloride) on the basis of powder diffraction data. The structure was refined following the flowchart by setting the initial values such that $S_{res}=1$, the target value=1 and the threshold value=1.01. As a result, it became possible to mechanically obtain a result of statistically feasible $\sigma_{Norm}=1.0088$.

FIG. 5A to FIG. 5I are diagrams illustrating examples of the crystal structure model in the embodiment while applying the restraint each time until the eighth cycle is executed. It is seen that the benzene ring is well shaped in the example in FIG. 5I by contribution of the restraint in comparison with the examples in FIG. 5A to FIG. 5C.

Figure 6:
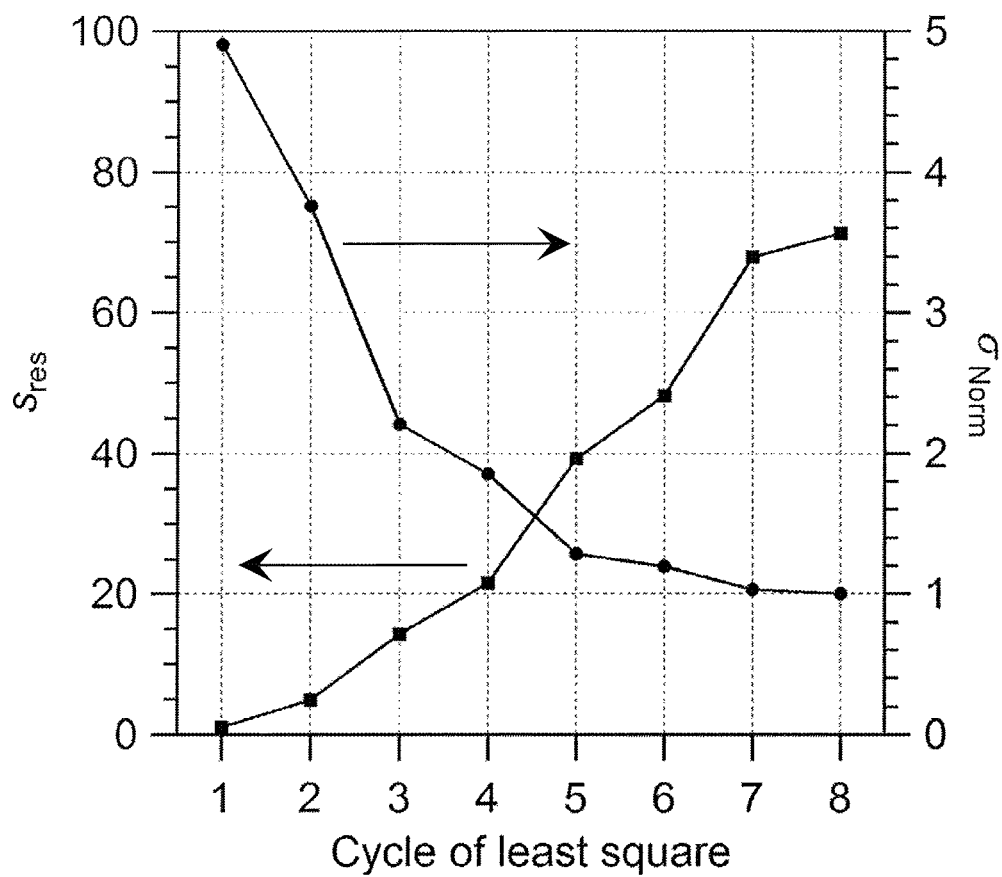
FIG. 6 is a diagram illustrating one example of transition of values of $s_{res}$ and $\sigma_{Norm}$ relative to the number of cycles.

FIG. 6 is a diagram illustrating one example of transition of $S_{res}$ and $\sigma_{Norm}$ relative to the number of cycles. It is seen that although $S_{res}$ increases from one to around 70, $\sigma_{Norm}$ rapidly decreases from around 5 and converges to one.

Figure 7:
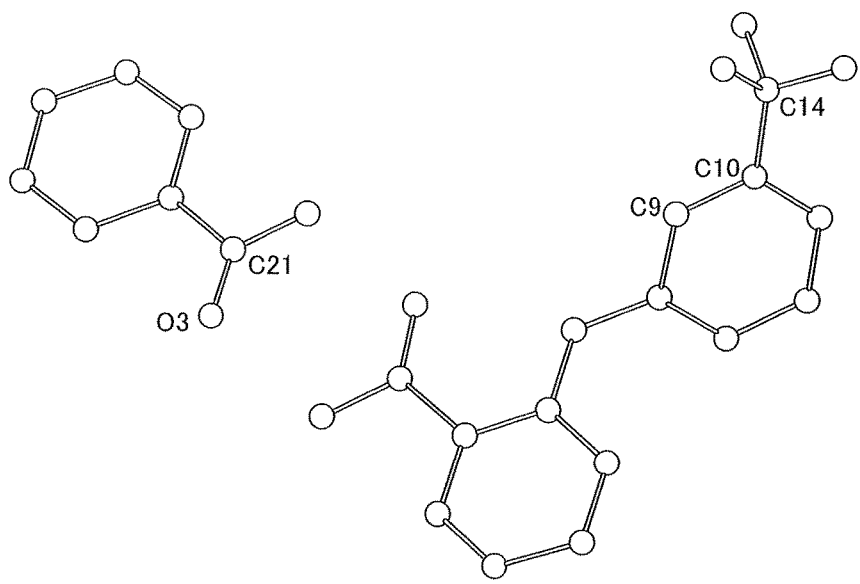
FIG. 7 is a diagram illustrating one example of a bond distance of O3-C21 and a bond angle of C9-C10-C14 in the crystal structure model of the embodiment.
Figure 8A:
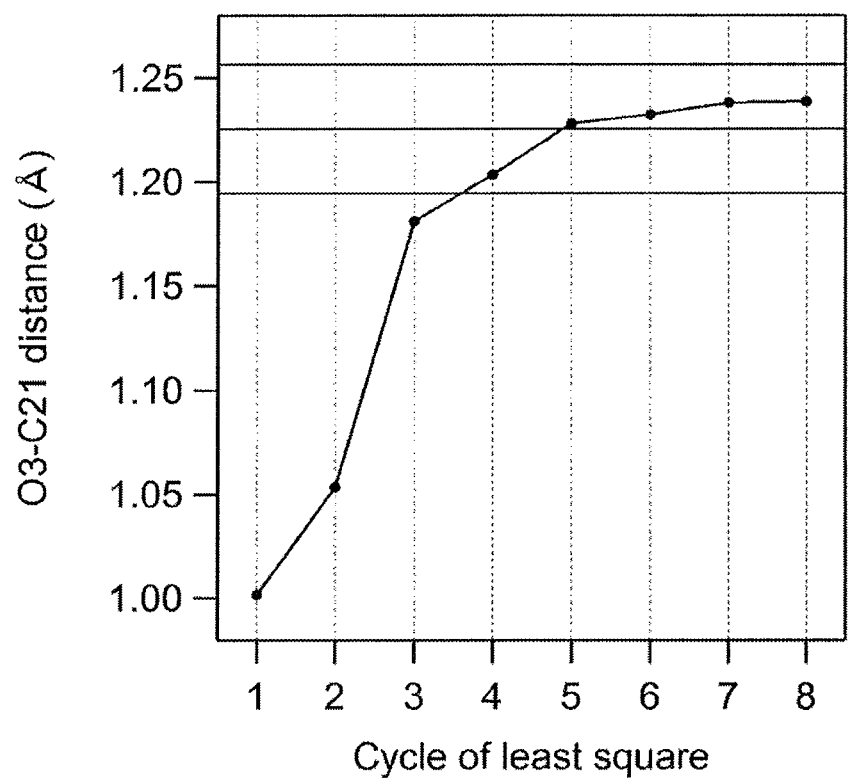
FIG. 8A is a graph illustrating one example of transition of the bond distance of O3-C21 relative to the number of cycles.
Figure 8B:
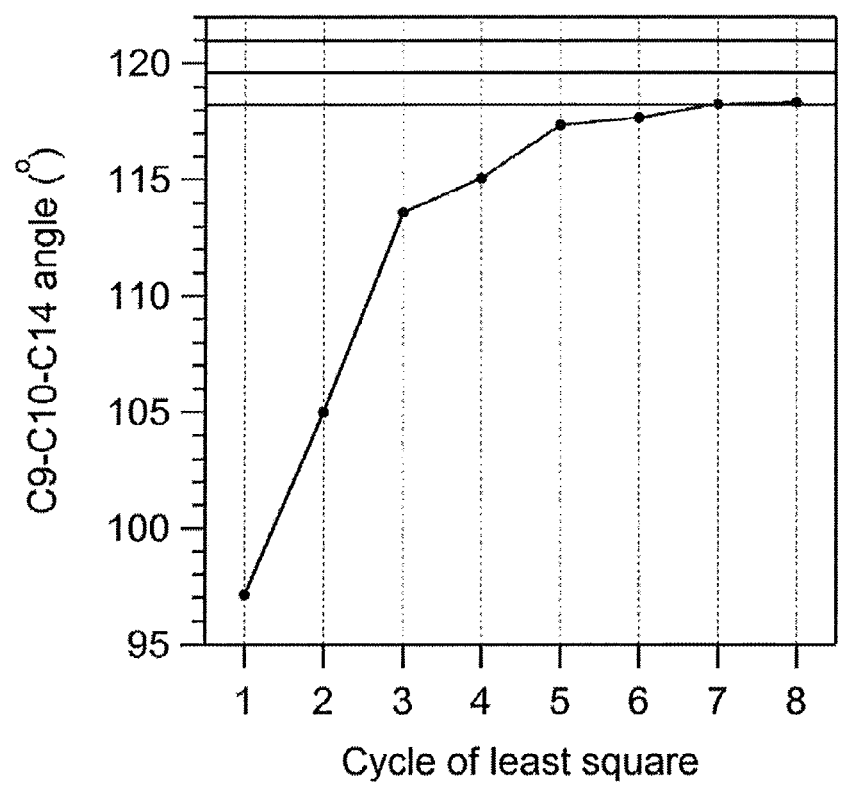
FIG. 8B is a graph illustrating one example of transition of the bond angle of C9-C10-C14 relative to the number of cycles.

Next, transition along the number of cycles was recorded focusing on specific bond distance and bond angle. FIG. 7 is a diagram illustrating examples of the bond distance of O3-C21 and the bond angle of C9-C10-C14 of the crystal structure model of the embodiment. FIG. 8A and FIG. 8B are graphs respectively illustrating examples of transition of the bond distance of O3-C21 and the bond angle of C9-C10-C14 relative to the number of cycles. FIG. 9 is a table illustrating one example of transition of the bond distance of O3-C21 and the bond angle of C9-C10-C14 relative to the number of cycles.

As illustrated in the drawings, the numerical values of both of the bond distance and the bond angle converge as the number of cycles is increased. However, values to which the bond distance and the bond angle have converged slightly diverge from their representative values though close to the representative values and are well-balanced reasonable values that also reflect the measured values sufficiently while the restraints are being appropriately applied thereto.

What is claimed is:

1. A structure refining apparatus which adjusts a crystal structure model on the basis of a measurement result and known data, comprising:
    a memory having stored instructions thereon; and
    a processor executing the instructions to:
    receive measurement data of a parameter,
    calculate various parameters specifying a crystal structure using a method of least squares for a total residual value, the total residual value having a first component calculated as a residual value between the measurement data and calculation data from the various parameters and a second component of a restraint residual value, the restraint residual value having a restraint term and a restraint coefficient and calculated as the residual value between a known representative value and the various parameters, the restraint coefficient having an initial value,
    calculate a normalized standard uncertainty value with the known representative value and the various parameters,
    compare the normalized standard uncertainty value to a target value,
    when the normalized standard uncertainty value is not within a predetermined range of the target value, update the restraint coefficient and use the updated restraint coefficient to recalculate the various parameters and the normalized standard uncertainty value,
    specify the crystal structure model on the basis of the calculated various parameters when the normalized standard uncertainty value is within a predetermined range, and
    output data on the specified crystal structure model.

2. The structure refining apparatus according to claim 1, wherein the restraint applying unit calculates normalized standard uncertainty value by normalizing the divergence between the parameter and the representative value by the standard uncertainty and determines contribution of a restraint term indicating a residual relative to the representative value so as to bring the normalized standard uncertainty value close to one, and
    wherein the structure specifying unit specifies the crystal structure model adapted to minimize the total residual value.

3. The structure refining apparatus according to claim 2, wherein the restraint applying unit determines contribution of the restraint term on the assumption that a divergence between the parameter and a known representative value relative to a standard uncertainty of the known representative value has a linear relation with contribution of the restraint term.

4. The structure refining apparatus according to claim 1, further comprising:
a representative value holding unit configured to acquire data on the representative value and a statistical uncertainty thereof from an external database through a network and to hold the data,
wherein the restraint applying unit calculates the restraint to be applied by using the held data on the representative value and the statistical uncertainty thereof.

5. A structure refining method which adjusts a crystal structure model on the basis of a measurement result and known data, comprising the steps of:
receiving measurement data of a parameter;
calculating various parameters specifying a crystal structure using a method of least squares for a total residual value, the total residual value having a first component calculated as a residual value between the measurement data and calculation data from the various parameters and a second component of a restraint residual value, the restraint residual value having a restraint term and a restraint coefficient and calculated as the residual value between a known representative value and the various parameters, the restraint coefficient having an initial value;
calculating a normalized standard uncertainty value with the known representative value and the various parameters;
comparing the normalized standard uncertainty value to a target value;
when the normalized standard uncertainty value is not within a predetermined range of the target value, update the restraint coefficient and use the updated restraint coefficient to recalculate the various parameters and the normalized standard uncertainty value;
specifying the crystal structure model on the basis of the calculated restraint coefficient when the normalized standard uncertainty value is within a predetermined range; and
outputting data on the specified crystal structure model.

6. A non-transitory computer-readable medium which records a program for structure refinement that adjusts a crystal structure model on the basis of a measurement result and known data,
the program causing a computer to execute a series of processes including the processes of:
receiving measurement data of a parameter;
calculating various parameters specifying a crystal structure using a method of least squares for a total residual value, the total residual value having a first component calculated as a residual value between the measurement data and calculation data from the various parameters and a second component of a restraint residual value, the restraint residual value having a restraint term and a restraint coefficient and calculated as the residual value between a known representative value and the various parameters, the restraint coefficient having an initial value;
calculating a normalized standard uncertainty value with the known representative value and the various parameters;
comparing the normalized standard uncertainty value to a target value;
when the normalized standard uncertainty value is not within a predetermined range of the target value, update the restraint coefficient and use the updated restraint coefficient to recalculate the various parameters and the normalized standard uncertainty value;
specifying the crystal structure model on the basis of the calculated restraint coefficient when the normalized standard uncertainty value is within a predetermined range; and
outputting data on the specified crystal structure model.

* * * * *